United States Patent [19]

Brüggemann et al.

[11] Patent Number: 5,763,067
[45] Date of Patent: Jun. 9, 1998

[54] LAYERED BODY FOR THE ABSORPTION OF LIQUIDS AND ITS PRODUCTION

[75] Inventors: Helmut Brüggemann, Duisburg; Kurt Dahmen, Mönchengladbach, both of Germany

[73] Assignee: Chemische Fabrik Stockhausen GmbH, Krefeld, Germany

[21] Appl. No.: 757,953

[22] Filed: Nov. 22, 1996

Related U.S. Application Data

[63] Continuation of Ser. No. 444,866, May 19, 1995, abandoned.

[30] Foreign Application Priority Data

May 26, 1994 [DE] Germany .................. 44 18 319.4

[51] Int. Cl.[6] ..................................................... B32B 5/22
[52] U.S. Cl. ................................ 428/317.9; 428/305.5; 428/316.6; 428/318.4; 604/367; 604/368; 604/369
[58] Field of Search .................... 428/305.5, 316.6, 428/317.9, 318.4; 604/367, 368, 369

[56] References Cited

U.S. PATENT DOCUMENTS

| | | |
|---|---|---|
| 4,235,237 | 11/1980 | Mesek et al. ............... 604/368 |
| 4,657,538 | 4/1987 | Becker et al. ............... 604/381 |
| 4,715,918 | 12/1987 | Lang . | |
| 4,806,408 | 2/1989 | Pierre et al. ............... 428/76 |
| 5,175,046 | 12/1992 | Nguyen . | |

FOREIGN PATENT DOCUMENTS

| | | |
|---|---|---|
| 0 427 219 | 5/1991 | European Pat. Off. . |
| 0 577 233 | 1/1994 | European Pat. Off. . |
| 42 33 289 | 4/1994 | Germany . |
| WO 87/03168 | 6/1987 | WIPO . |

OTHER PUBLICATIONS

Translation of a draft response to the European Patent Office in the matter of PCT/EP95/01926, passages D1 to D5.

*Primary Examiner*—Kathleen Choi
*Attorney, Agent, or Firm*—Oblon, Spivak, McClelland, Maier & Neustadt, P.C.

[57] ABSTRACT

The present invention relates to layered bodies consisting of at least one plastic foam and/or latex foam layer and particulate, superabsorbent polymers for the absorption of water and aqueous liquids, which bodies comprise the superabsorber on, between, or below the foamed plastic and/or latex layer in a quantitatively and/or locally predetermined and fixed area, configuration at a quantity ratio of plastic and/or latex foam to the superabsorber of 1:500 to 50:1. The plastic/latex foam may comprise fillers, pigments and/or synthetic fibers. The layered bodies have an increased absorption capacity for water and aqueous liquids, in particular under load. They are manufactured by spreading out the foam, applying the superabsorber in the predetermined quantity ratio, optionally by using a stencil, and by fixing it by means of a heat treatment. These layered bodies are used in hygienic articles, as components in natural or artificial soils, as insulating material for pipes and ducts, primarily for cables and constructional elements, as liquid-absorbing and liquid-storing component in packaging materials, and as a part in garments.

18 Claims, 1 Drawing Sheet

LAYERED BODY FOR THE ABSORPTION OF LIQUIDS AND ITS PRODUCTION

This application is a continuation of application Ser. No. 08/444,866, filed on May 19, 1995, now abandoned.

The present invention relates to bodies that absorb water and aqueous liquids and which consist of foamed plastic and latex layers and superabsorbent polymers. The present invention further relates to a process for producing these bodies and to their use as absorbents, particularly in hygienics for the absorption of body fluids, such as blood, sweat, urine, and other liquid excretions. Additionally, the present invention relates to the use of these bodies as components in wound dressings, in packaging and insulating materials, in textiles for clothing and cleaning purposes, and to their use in the cultivation of plants.

Substances having a layered structure and the capacity of absorbing aqueous liquids have been known for some time. U.S. Pat. No. 4,000,028 describes materials of latex foam and cellulose fluff, but not comprising superabsorbent polymers; thus they have a very limited capability of absorbing liquids.

U.S. Pat. No. 5,128,082 describes absorbents produced from mixtures of fluff materials and superabsorbent polymers and a surrounding latex forming the outer layer. The fluff portion largely prevents the contact between polymer and latex. The polymer portion in these bodies is not distributed in a uniform manner; this results in the known difficulties with respect to the absorption of liquids connected with the disadvantages regarding the wearing behavior of these hygienic articles.

EP 0 212 618 B1 describes diaper constructions wherein these disadvantages are avoided by the fact that the polymers which have a certain particle-size distribution are distributed in the cellulose fiber layer by using a gradient. However, such constructions are insufficiently stable; in particular the distribution of the materials changes during the transport.

In general, the mixing of superabsorbent polymers with watery latex foams results in the fact that the foams collapse under water removal; this destroys the open-cell structure with the consequence that only the superficial polymer particles are capable of absorbing liquids.

Mixtures of superabsorbent polymers and latex foams are known from EP 0 427 219 A2; these are obtained by introducing the polymers into the foamed latex in the form of a powder spray. This method does not permit a defined construction of these bodies; in particular, an accurate distribution of the polymers is not possible.

The use of a tape as a component for the insulation of electric cables is known from EP 0 577 233 A1. This tape consists of a non-woven fabric layer and a foam layer, and it comprises particles of a swelling powder anchored in the region of the non-woven layer.

U.S. Pat. No. 4,649,164 describes foamed water-absorbing materials formed of $CO_2$-releasing blowing agents and acrylate-(meth)acrylic acid latices; here the foamed latex itself represents the absorbent material. Owing to the hydrophobic nature of the acrylate component, the absorption capacity of these foams—as compared to the known superabsorbers—is limited.

Biocompatible, open-cell polyurethane foams that can be used as wound dressing and which have guar gum as incorporated hydrogel are also known from DE 42 42 015 A1. The gel component is foamed in situ during the production. The water absorption capacity of these products is to be limited to a value below the triple of the initial weight.

EP 0 340 945 A1 describes mixtures of elastomers and water-swellable hydrocolloids, which are cationic and preferably chitosan salts, for the use as wound dressings having absorption values of at least 180%-wt.; the colloidal particles are randomly integrated in the elastomer, and the absorption capacity for aqueous liquids is also limited.

Similar hydrophilic polyurethane foam gels are known from DE 42 33 289 A1; these are produced from mixtures of polyols, diisocyanates and superabsorbent polymers, the superabsorbent polymer being evenly incorporated in the foam owing to the production-specific mixing of the components. The products are used as wound dressings having a defined adherence.

Additionally, U.S. Pat. No. 5,149,339 describes absorbent constructions comprising superabsorbent powdery polymers in fiber-containing, adjacent, cellular structures of these constructions; however, the polymer is present therein in a dense and unfixed packing configuration.

Accordingly, there was the object to provide a body that is based on layered absorbent materials for water and aqueous liquids, and which avoids the above-mentioned disadvantages.

This object could be achieved by a layered body of at least one open-cell layer of plastic and/or latex foam and at least one layer formed of a particulate, superabsorbent polymer, wherein the layered body comprises the amount of superabsorbent polymer in a defined distribution and fixed at the boundary surface of the foam layer.

Accordingly, the subject matter of the present invention is a layered body consisting of one or several plastic foam layers and/or latex foam layers and particulate, superabsorbent polymers for the absorption of water and aqueous liquids, which is characterized in that the superabsorbent polymer is comprised directly on, between, or below the foamed plastic and/or foamed latex layers in a quantitatively and/or locally predetermined and fixed area configuration, and that the quantity ratio of foamed plastic and/or foamed latex layer to the superabsorbent polymer amounts to 1:500 to 50:1, preferably 1:50 to 25:1, and most preferably 1:5 to 10:1. The layered absorbent body may be rigid or flexible.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1A:
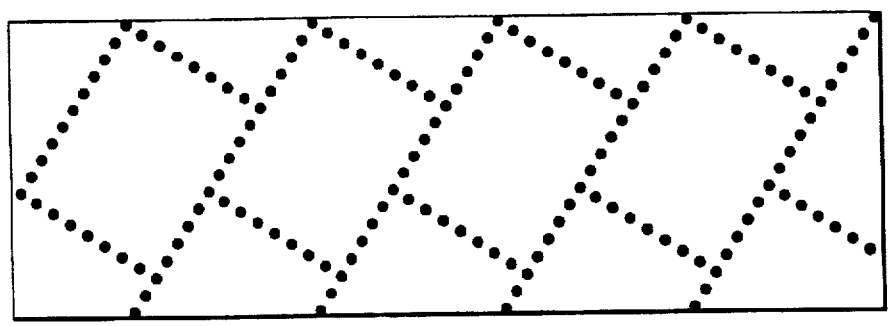
FIG. 1 shows an embodiment of the layered absorbent body of the present invention in which superabsorber particles are fixedly attached to a layer of foam.

Most surprisingly, the swelling capacity of the polymer remains unaffected during the absorption using the layered body according to the present invention, although the plastic material or the latex and the polymer are in direct contact; for this reason, the polymer's absorption capacity for aqueous liquids is also maintained in the chosen configuration.

When a 0.9% NaCl-solution is used, the layered absorbent body according to the present invention preferably has a retention of at least 0.1 liter/$M^2$ surface, a maximum absorption of at least 0.1 liter/$m^2$ surface, and an absorption under load (AUL) of at least 2 g/g at 0.021 Pa.

Another subject matter of the present invention is a manufacturing process and the use of the layered absorbent bodies according to the present invention. The process for the production is characterized in that at least a) one plastic foam and/or latex foam having a weight per liter of 50 to 1,000 g/l is formed and the preferably open-cell foam is spread out over the surface at a layer thickness of 1 µm to 100,000 µm, preferably of 10 µm to 10,000 µm, and most preferably of 200 µm to 5,000 µm, b) the superabsorbent, particulate polymer is applied on the spread-out foam at a quantity ratio of foamed plastic and/or foamed latex layer to the superabsorbent polymer of 1:500 to 50:1, preferably 1:50 to 25:1, and most preferably 1:5 to 10:1, optionally by using at least one stencil, perforated disk, and/or sieve, at a quantitatively and superficially defined distribution, is optionally fixed by a heat treatment, wherein process step a) and/or b) is optionally repeated in desired succession, and that finally a heat treatment under cross-linkage of the foamed layers is carried out.

The production of the absorbent body according to the present invention is effected by using known raw materials. A suitable basis for the plastic or latex foam layer are commercial plastic materials and/or latex dispersions for rigid, semirigid, flexible, and nonrigid plastic foams of polystyrene, styrene copolymers, rigid and flexible PVC, polycarbonates, polycarboimides, polymethacrylimides, polyamides, polystyrene-butadiene-polymers, as well as of phenolic and urea resins; preferably copolymers which are formed of at least two monomers of (meth)acrylates, styrene, butadiene, vinyl acetate, and the vinyl acetates completely or partially saponified to the polymerized vinyl alcohol units.

The plastic foam and/or latex foam is formed by using known means, for example, by intense stirring or mixing under mixing with air, in general under the addition of foaming aids.

The kind and amount of the used plastic or latex material determines in known manner the mechanical properties of the bodies according to the present invention, e.g., the degree of flexibility and the surface behavior of the constructions.

It has been found that the properties may be influenced by mixing the plastic and latex materials. The absorption rate for water or aqueous liquids is determined to a large extent by the kind of the used plastic and/or latex material. In particular, it has surprisingly been found that mixing these components improves the absorption rate in certain cases to such an extent that it is above the value of absorbent substances formed of only one plastic or latex component.

Also, it is most surprising that the absorption speed is considerably influenced by the kind and amount as well as by the distribution of the additionally used filling materials. Suitable fillers are chalks, bentonites; silica gels and silicic acid; activated carbons, pigments, such as titanium dioxide and iron oxide; as well as natural and/or synthetic fibrous materials, such as viscose and cotton fibers and fabrics, and/or polyester and polyamide fibers, and mixtures of different fibers or corresponding fabrics. Additionally suitable are finely ground plastics, in particular those of the same kind as the used plastic or latex material. The kind, concentration, and distribution of the filler may be the same or different in each foam layer. Mixtures of different fillers may also be used. The single foam layer may have a degree of filling ranging from 0 to 1,000%-wt., relative to the amount of plastic material or latex, preferably it amounts to a maximum of 400%-wt., and most preferably to a maximum of 200%-wt. Furthermore, the described fillers may also be introduced into the absorbent body as a separate layer. The superabsorbent polymer may also be applied in admixture with the materials mentioned as suitable fillers.

The plastic or latex dispersion may also be employed by using further additives, such as blowing or foaming agents, foam stabilizers, cross-linking or vulcanizing agents; the processing conditions for the production and stabilization of such foams are known.

The latex foam may be formed in different geometric forms, the formation of an open-cell foam layer having an arbitrary thickness being preferred. As described in U.S. Pat. No. 4,000,028, surfaces removable from auxiliary supports may temporarily be used for the production for example, metallic strips and sheets, silicone paper, glass fibers, glass surfaces, or textile fabrics; according to the present invention it is preferred that surfaces of materials becoming a component of the absorbent body be used as a base, for example, plastic films and non-woven fabrics which are permeable and impermeable to liquids, cellulose or paper layers, or textile fabrics.

The basic layer may also consist of the unexpanded plastic or latex material; it is spread as a thickened dispersion and cured to form a homogeneous, liquid-impermeable layer. Unless other materials, such as fillers or the particulate polymer itself, are used for this purpose, the materials mentioned as suitable basis or a foam layer may serve to cover the last-applied layer.

According to the present invention, the particulate superabsorbent polymers may consist of water-insoluble, water-swellable polymers and copolymers of monomer units of (meth)acrylic acid, maleic acid, itaconic acid and their anhydrides and salts; fumaric acid and its salts, in particular its alkali, alkaline earth, and ammonium salts; (meth) acrylamide, (meth)acrylonitrile, and vinyl acetate and its hydrolysis products; vinylpryrrolidone, vinylpyridine, vinylsulfonic acid and its esters and amides; as well as of N-alkyl and N,N-di-alkyl-substituted esters and/or amides of (meth)acrylic acid and their salts and/or their quaternary ammonium compounds. Also suitable are natural water-swellable polymers, such as carboxymethylcellulose, hydroxyethylcellulose, guar flour, xanthans, alginates, starch, and their derivatives, as well as graft polymers of these substances and of the mentioned monomers or mixtures of the above-mentioned polymers with these substances.

The particulate, superabsorbent polymer is applied on the previously manufactured surface of the plastic or latex foam layer in distributed form as a powder having a particle-size distribution ranging from 1 µm to 20,000 µm. This may done, for example, by sprinkling the powder from suitable containers or by means of suitable devices.

The particle size of the powders depends on the application of the absorbent bodies. In hygienics, it is preferred that powders having grain sizes ranging between 50 µm and 1,000 µm be used, whereas a range below 400 µm is chosen when they are to be used in cable insulation.

The bodies according to the present invention comprise finest grain portions of the superabsorbent polymers in an only very small amount, with exactly these particles being fixed in the surface region of the foam layer. In handling the bodies according to the present invention, continued formation of finest polymer particles is avoided owing to mechanical processes.

According to a special embodiment, the amount and the powder distribution relative to the surface unit may be such that only certain surface regions of the foam layer are coated and/or that the surfaces are covered with differing amounts. To this end, application may be effected by using stencils, perforated disks, screens, or suitable combinations thereof, optionally under particle size classification of the polymers. For instance, the application of fine-grained powders may provide a liquid-blocking layer, or—in contrast to this—the application of coarse-grained polymer portions may achieve an improved distribution of the liquid.

The amount, particle size, and distribution of the particulate, superabsorbent polymer on the individual foamed plastic layers and/or foamed latex layers may be different.

The layer concentration of the plastic and/or latex foam surface is in the range of from 0.1 g to 500 g of the particulate, superabsorbent polymer, relative to one square meter of the foamed surface of the body, preferably in the range of 10 to 300 g/m², and most preferably in the range of 50 to 200 g/m².

The superabsorbent polymer portion in the total construction of the absorbent body amounts to 15–99%-wt., preferably 40–90%-wt., and most preferably 50–80%-wt.

The absorbent body material is manufactured by applying one or several plastic and/or latex foam layers alternating with applying the particulate superabsorber on the previously formed layer. To facilitate further processing, the plastic or latex foam layer may completely or partially be vulcanized under suitable known conditions, such as by single or multiple heating, for example in the IR-field or by treatment in the UV-field, after each application of the polymer; or the same may be done with the foam using other known measures. By means of differently applying the polymer particles on or into the individual layers, bodies are manufactured wherein the absorbent polymer is distributed with a certain gradient. Finally, a vulcanization is effected to completely cross-link the plastic or latex layers; this may be connected with additionally drying the body.

Figure 1B:
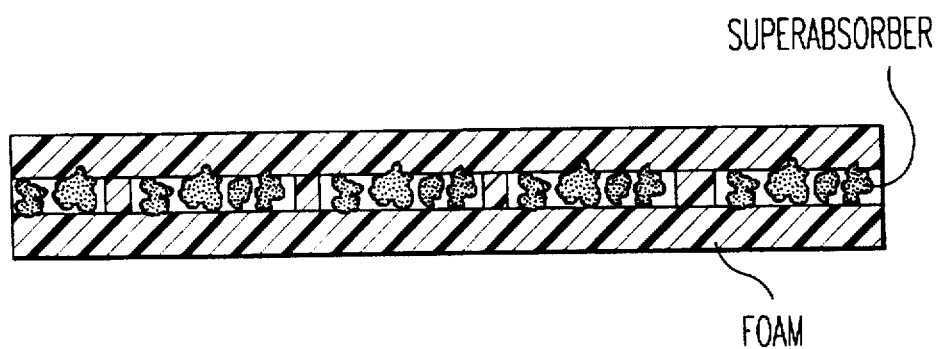

Optionally, the body according to the present invention may finally be processed with a calendar and/or an embossing roll. A preferred example of the absorbent body according to the present invention is shown in FIG. 1.

The bodies according to the present invention can be used for the absorption of water and various kinds of aqueous liquids. In particular, they are used directly, or as a component of or additive in articles used in the hygienic and personal field, e.g., in diapers, tampons, and incontinence articles, and in sanitary articles for wound dressing. Additionally, the absorbent bodies are suitable as plant growth medium storing water and aqueous solutions; for the storage and transport of plants and parts of plants; for the insulation of pipes and ducts, in particular for electric and light transmitting cables; and as component of constructional elements, e.g., for the insulation of outer walls; and as packaging material or packaging component for commercial goods, in particular for foodstuffs and beverages. In addition, they may be incorporated into articles of clothing to improve the wearing property.

The properties of the bodies according to the present invention which absorb water and aqueous liquids may be determined by means of the following test methods.

Test methods:

A. Tea bag test (TBT)

To determine the absorption capacity, the TBT was carried out. A 0.9% NaCl-solution was used as test solution (unless stated otherwise).

In accordance with the superabsorbent polymer layer given by production, a piece of material was punched out of the absorbent body, it comprises 0.2 g of the superabsorbent polymer (SAP). The piece is weighed into a tea bag. Subsequently, the tea bag is placed into the test solution for 10 minutes. After dripping for 5 minutes, the tea bag was weighed and then centrifuged in a centrifuge (commercial spin dryer, 1,400 rpm). Then weighing was effected again.

The liquid absorption is expressed either in terms of 1 g of the body, 1 g of SAP used, or in terms of 1 m² of the body.

B. Absorption under Load (AUL)

To determine the liquid absorption capacity under load, the "absorption under load" (AUL)—as described in EP-A-0 339 461—was determined. Deviating from this instruction, a circular piece of the superabsorbent body having the size of the inner diameter of the AUL-crucible was used as test substance. The liquid absorption is expressed either in terms of 1 g of the body, 1 g of the SAP used, or in terms of 1 m² of the body surface.

C. Demand-Absorbency-Test

To determine another application technological property, the absorption of model urine is carried out according to the "Demand Absorbency Test" (DAT) (W. F. Schlauch, lecture index 1978, Amsterdam, DE 39 17 646) and the absorption rate determined. The measuring device consists of a burette filled with the model urine solution (2.0% urea, 0.9% NaCl, 0.1% $MgSO_4$, and 0.06% $CaCl_2$, dissolved in dist. water) and a test desk provided with an outlet for the model urine solution, which is connected to the measuring burette. On the test desk, a piece of the body according to the present invention comprising 1 g of the SAP is placed in the center of the liquid outlet. Then the model urine solution is brought into contact with the test substance by slight pressure on the connection hose. The liquid absorption, read at the burette, is noted after each minute. Once 50 ml of the test solution have been absorbed, the required time is noted.

A second test (DATP) is carried out in the same manner; however, the test piece is loaded with a pressure (0.3 psi). The values are read off and noted down in the same manner.

D. Inclined-Plane-Test

The "inclined-plane-test" to determine the absorption properties of the bodies according to the present invention is conducted following the test method specified in EP 0 546 587 A1. A piece of the absorbent body according to the present invention, 10 cm×30 cm in size, is attached to an inclined plane (angle of inclination: 45°) in the longitudinal direction. At a flow rate of 4 ml/sec., 100 ml of a 0.9% NaCl-solution are placed in the middle of the upper edge of the test body by means of a drop funnel. The liquid flowing over the surface of the test body is immediately collected in a catch-pot 1 and measured. The total amount of liquid flown from the surface of the collector 1 and out of the test body into the collector 2 is determined after 10 min. This procedure is repeated until the absorption capacity of the test body is exhausted—in general after the 4th or 5th application of liquid.

The test result is expressed as follows:

1) the liquid amount run down the surface and collected in the collector 1 (OA), 2) the time until the liquid discharges at the lower edge of the test body (ZA), and 3) the total amount of liquid collected after 10 minutes in the drip trays 1 and 2 (AV).

The present invention will be illustrated in greater detail by means of the following Examples.

The products used for the production of the plastic and/or latex foam layers are referred to in the following only by their commercial names and are characterized according to their chemical composition:

| | |
|---|---|
| Estekoll ® HL 40 | acrylic ester |
| Estekoll ® 60 | vinyl copolymer |
| Estekoll ® SU 390 | acrylic-acid ester copolymer |
| Fixamin ® PU 603 | polyurethane/polyester (without free isocyanate groups) |
| Fixamin ® PU 421 | polyurethane (aliphatic) |

-continued

| | |
|---|---|
| Fixamin ® PUK | polyester polyurethane |
| Fixamin ® PU 555 | polyester polyurethane (without free isocyanate groups) |
| Sarpifan ® CAW | vinyl copolymer (plasticized) |
| Sarpifan ® DFP | vinyl copolymer (plasticized) |
| Sarpifan ® BKF | polyvinyl acetate (unplasticized) |
| Sarpifan ® HP 79 | vinyl copolymer (unplasticized) |
| Sarpifan ® NL | nitrile-rubber latex |
| Sarpifan ® U 75 | acrylic acid copolymer |
| Sarpifan ® VT | acrylic-acid ester copolymer |
| Sarpifan ® VB | acrylic ester |
| Sarpifan ® WRG | acrylic ester |
| Sarpifan ® VBA | butadiene copolymer |
| Stokal ® STD | ammonium stearate |
| Mirox ® TA | potassium polyacrylate |
| Lavoral ® LO | fatty alcohol sulfate |
| Favor ® SAB 922 FAF | loosely cross-linked, partially neutralized polyacrylate |
| Favor ® SAB 990 | loosely cross-linked, partially neutralized polyacrylate |
| Favor ® 922 SK | loosely cross-linked, partially neutralized polyacrylate |
| Plantaren ® 2000 CS/UP | alkyl polyglycoside |
| Favor ® SXM 75 | loosely cross-linked, partially neutralized polyacrylate |
| Favor ® SXM 100 | loosely cross-linked, partially neutralized polyacrylate |
| Bunatex ® SL 3510 | styrene/butadiene copolymer |
| Bunatex ® SL 2810 | styrene/butadiene copolymer |
| Acronal ® DS 2331 X | copolymer based on ethyl acrylate |
| Kaolin ® W | chalk mineral |
| Neogel ® V 70 ZB | vulcanizing paste based on sulfur |
| Neogel ® V 77 ZB | vulcanizing paste based on sulfur |
| Calcicoll ® W 12 | partially crystalline chalk |
| Fixapet ® VNF | nitrogen-containing, formaldehyde-free cross-linking agent |
| Vinipas ® LL 778/5 | ethylene/vinyl acetate copolymer |
| Lipolan ® VD 9910 | butadiene/styrene copolymer |
| Litex ® AP 4120 | butyl acrylate/styrene copolymer |

EXAMPLES 1–4

80 parts of Fixamin®PUK, 3 parts of Stokal®STD, 5 parts of Mirox ®TA, 11 parts of deionized water, and 1 part of Lavoral®LO were mixed and foamed with a hand mixer to a foam weight per liter of 250 g/l.

The foam was knife coated onto a gray cotton cloth (layer thickness: 1.5 mm); then an extreme excess of 500 g/m² of the superabsorbent polymer (SAP) was sprinkled thereon. Heating to 100° C. in the drying oven for 6 min. followed; subsequently the samples were calendered and the nonadhering SAP was thrown off. Again, heating of the samples to 170° C. for 5 min.

| | SAP [kind] | (max.) [l/m²] | (ret.) [l/m²] |
|---|---|---|---|
| | | Tea bag test | |
| Example 1 | Favor ® SAB 922 FAF | 1.9 | 1.4 |
| Example 2 | Favor ® SAB 990 | 6.8 | 4.9 |
| Example 3 | Favor ® 922 SK | 9.6 | 8.2 |
| Example 4 | carboxymethylcellulose (acc. to Ex. 2 No. 50 in EP 053 8904 A2) | 3.8 | 1.5 |

Comparative Examples 1–4

Procedure as in Examples 1–4, except that the foam was mixed with the SAP, and the mass so obtained was spread on gray cotton cloth (thickness about 3 mm). Afterwards the procedure corresponded to Examples 1–4.

None of the examined samples showed an absorption (TBT) of more than 0.2 l/m².

Comparative Examples 5 and 6

20g Caradol 48-2 (polyol of Shell), 0.2 g Tedostab (polysiloxane of Goldschmidt), 0.08 g dibutyltin dilaurate, and 0.08 g N,N-dimethylaminoethanol are mixed. Favor SXM 100 is added to this mixture. Then, a mixture of 1 g of water and 10 g of toluylene diisocyanate is added under stirring. The mixture is poured on a polyethylene film. After 2 hours, the polyurethane foam is cured. The white, moderately flexible structure has a thickness of about 5 mm.

| | | TBT (ret.)* | |
|---|---|---|---|
| Comparative Example | Favor SXM 100 (g) | (30 sec) (g/g) | (30 min) (g/g) |
| 5 | 15.68 | 4.5 | 12.0 |
| 6 | 7.84 | 3.1 | 9.70 |

*The measured values relate to the superabsorber used.

EXAMPLE 5

A foam was prepared as in Examples 1–4. This foam was applied on a gray cotton cloth at a layer thickness of 1.5 mm. Then a screen was placed on the foam. The free foam squares were sprinkled with Favor®SAB 990 (surface concentration 150 g/m², relative to the total surface). Subsequently, the screen was removed and a cover layer of 1 mm of the described latex foam was applied. The foam was then treated as in Examples 1–4. TBT* (max.): 6.5 l/M² TBT* (ret.): 5.0 l/m².

*In this case the measurement of the TBT was carried out as follows: One of the resulting bags was cut out of the manufactured body. This bag was then used for measuring the absorption values without enclosing it into a tea bag.

EXAMPLE 6 AND 7

The procedure of Example 5 is repeated; however, a cross-linked guar flour is used instead of Favor SAP 990. The polymer foam is cross-linked at 120° C. for 30/60 mins. (Example 6/7). The absorption values were determined in dependence on the dipping time:

| | Dipping time [min.] | Tea bag test | |
|---|---|---|---|
| | | max. [g/g SAP] | ret. [g/g SAP] |
| Example 6 | 1 | 5.9 | 7.3 |
| | 10 | 15.0 | 14.9 |
| | 60 | 15.7 | 16.3 |
| | 240 | 16.7 | 17.3 |
| Example 7 | 1 | 7.3 | 9.0 |
| | 10 | 13.2 | 11.1 |
| | 30 | 14.6 | 11.8 |
| | 60 | 14.6 | 13.5 |
| | 240 | 15.9 | 15.2 |

EXAMPLES 8–10

In the manner described, a foam is prepared using 0.8 g of Plantaren®2000 CS/UP, 1 g of Stokal®SR, 0.2 g of guar flour 104, 3 g of Fixamin®PUK, 15 g of Sarpifan®VBA, and 10 g of deionized water. The foam is expanded to a total volume of 400 ml and evenly distributed over a surface of 0.1 m². Subsequently, 30 g of a SAP is evenly distributed on this area. The mass so obtained is oven-dried at 160° C. for 5 minutes. Then, the same foam layer is applied on this mass, sprinkled again with the same amount of SAP, and dried again at 160° C. for 5 minutes. This procedure is repeated for two more times in Examples 8 and 9. Subsequently, a last foam layer is applied, and the obtained body is heated at 160° C. in the drying oven for 5 minutes without any additional sprinking.

|  | SAP (kind) | TBT (max.) [l/m²] | TBT (ret.) [l/m²] |
| --- | --- | --- | --- |
| Example 8 | Favor ® SXM 75 | 53 | 36 |
| Example 9 | Favor ® 922 FAF | 59 | 46 |
| Example 10* | Favor ® 922 FAF | 31 | 22 |

*40 g/m² of polyamide fiber (NC 0261) is additionally incorporated into each absorbent layer.

EXAMPLE 11

0.8 g of Plantaren®2000 CS/UP, 0.4 g of Stokal®SR, 8 of deionized water, and 13.8 g of Fixamin®PU 421 are expanded (foam weight per liter about 300 g/l), distributed on a metal plate having a size of 460 cm², and heated to 160° C. for 10 minutes. Subsequently, a foam of 0.4 g of Plantaren®2000 CS/UP, 0.4 g of Stokal®SR, 6 g of deionized water, and 4.9 g of Estekoll®SU 390 is prepared (foam weight per liter as before) and applied on the existing foam layer. This foam layer is sprinkled with 13.8 g of Favor®SXM 75 and then heated under the above-mentioned conditions. Subsequently, another layer of the second foam is applied, sprinkled again with the same amount of the same SAP, and subjected to a thermal aftertreatment. The same foam layer is applied once more; however, this is not sprinkled with SAP. After having been heated again to 160° C. (10 minutes), the resultant body is provided with a cover layer of the above-mentioned formulation and heated again. Then the soft and flexible body thus obtained is removed from the metal surface.

TBT (max./ret.): 25/16.6 [l/m²]

EXAMPLES 12–16

A foam having a volume of about 0.8 l is expanded using 2 g of Plantaren®2000 CS/UP, 2 g of Stokal®SR, 5 g of Fixamin®PUK, 26 g of Sarpifan®VBA, 5 g of Estekol ®60, and 20 g of deionized water.

The foam is divided in 2 halves. The first half is spread out over a plate on an area of 0.1 m²; subsequently, the SAP Favor®SXM 75 is evenly sprinkled on this area in a defined amount which is listed in the following Table. This mass is then dried at 160° C. for 5 minutes, covered with the second half of the expanded foam, and dried again under the same conditions. The substance so obtained is removed from the plate and examined with respect to its absorption capacity.

|  |  | Tea bag test (10') | |
| --- | --- | --- | --- |
| Example | Amount of sprinkled SAP [g/m²] | (max.) [l/m²] | (ret.) [l/m²] |
| 12 | 150 | 10.2 | 6.1 |
| 13 | 200 | 11.6 | 7.3 |
| 14 | 250 | 14.7 | 9.9 |
| 15 | 300 | 16.0 | 10.5 |
| 16 | 400 | 18.2 | 11.4 |

EXAMPLE 17, 18

1 g of Plantaren®2000 CS/UP, 1 g of Stokal®SR, 12 g of Sarpifan®VBA, 6 g of Fixamin®PUK, and 10 g of deionized water are expanded as described above and spread out over a plate on an area of 0.1 m² (base layer). The mass is sprinkled with a mixture of 30 g of Favor®SAB 990, and 0.3 g of polyamide fiber and then dried at 150° C. for 5 minutes. Subsequently, a foam of 0.8 g of Plantaren®2000 CS/PU, 0.8 g of Stokal®SR, 6.7 g of Sarpifan®VBA, 3.1 g of Estekoll® SU 390, and 10 g of deionized water, expanded to about 400 ml, is spread out. This layer is also sprinkled with the above amounts of Favor® SAB 990 and polyamide fiber and dried at 150° C. for 5 minutes. Two more of the minutes same layers are applied. Then this body is provided with a cover layer which corresponds to the base layer.

In another test (Example 18) the above test was repeated, except that 1.5 g of Fixamin®PUK and 16.59 g of Sarpifan®VBA were used for the cover layer and base layer.

The absorption values after one and 10 minutes and the AUL-value were determined in these Examples. The values were based on the amount of SAP used.

|  | TBT (1 minute) | | TBT (10 minutes) | | |
| --- | --- | --- | --- | --- | --- |
| Example | (max.) [g/g] | (ret.) [g/g] | (max.) [g/g] | (ret.) [g/g] | AUL [g/g] |
| 17 | 20.4 | 18.9 | 41.8 | 28.0 | 24.4 |
| 18 | 19.8 | 18.2 | 44.0 | 28.8 | 25.6 |

COMPARATIVE EXAMPLES 5, 6

Examples 17 and 18 were repeated without the addition of an SAP. The obtained absorption values were expressed in terms of 1 g of the body.

|  | TBT (10 minutes) | | |
| --- | --- | --- | --- |
| Comparative Example | (max.) [g/g] | (ret.) [g/g] | AUL [g/g] |
| 5 | 1.2 | 0.5 | 1.3 |
| 6 | 7.3 | 0.7 | 4.0 |

EXAMPLES 19–33

Another dispersion (see Table) is added to a mixture of 0.8 g of Plantaren®2000 CS/UP, 0.8 g of Stokal® SR, 9.4 g of Sarpifan®VBA, and 10 g of water. A foam is prepared thereof and spread on 0.1 m², sprinkled with 20 g of Favor®SXM 75, and subsequently dried at 150° C. for 5 minutes. The semi foam layer as above is spread on the body thus obtained; subsequently, 10 g of the mentioned SAP are sprinkled and dried as described above. Two more foam layers having the above-mentioned formulation are then applied on this mass; the last one is covered with a paper web (Kleenex).

| Example [No.] | Dispersion TBT [Kind] | [Amount] [g] | DAT [1 min.] [g/g] | DAT (max.) [Amount] [g/g] | DAT (max.) [Time] [sec.] | DATP [1 min.] [g/g] | DATP (max.) [Amount] [g/g] | DATP (max.) [Time] [sec.] | [max.] [g/g] | [ret.] [g/g] |
|---|---|---|---|---|---|---|---|---|---|---|
| 19 | Estekoll ® 60 | 3.35 | 14.0 | 29.5 | 455 | 3.3 | 22.7 | 1285 | 18.5 | 10.2 |
| 20 | Estekoll ® HL 40 | 3.66 | 14.2 | 30.0 | 505 | 5.6 | 22.6 | 1155 | 17.8 | 10.3 |
| 21 | Fixamin ® PU 421 | 4.67 | 11.9 | 22.0 | 475 | 3.8 | 22.1 | 1520 | 14.8 | 10.1 |
| 22 | Fixamin ® PUK | 4.02 | 13.1 | 27.0 | 590 | 3.1 | 22.2 | 1390 | 15.2 | 10.0 |
| 23 | Fixamin ® PU 555 | 6.70 | 12.0 | 25.0 | 505 | 6.2 | 23.6 | 815 | 14.5 | 9.9 |
| 24 | Sarpifan ® BKF | 4.02 | 13.9 | 26.3 | 540 | 2.3 | 21.5 | 1950 | 15.7 | 10.1 |
| 25 | Sarpifan ® CAW | 4.02 | 14.2 | 28.3 | 465 | 3.4 | 20.1 | 1315 | 16.0 | 10.3 |
| 26 | Sarpifan ® DFP | 3.35 | 12.8 | 26.7 | 600 | 2.9 | 24.5 | 1480 | 17.5 | 10.2 |
| 27 | Sarpifan ® HP79 | 3.87 | 13.7 | 27.1 | 540 | 3.7 | 28.1 | 1240 | 18.4 | 10.2 |
| 28 | Sarpifan ® MKD | 4.02 | 13.1 | 27.7 | 620 | 4.5 | 27.0 | 990 | 16.4 | 10.0 |
| 29 | Sarpifan ® NL | 4.47 | 13.9 | 25.2 | 550 | 2.9 | 24.1 | 1325 | 17.5 | 9.8 |
| 30 | Sarpifan ® U 75 | 4.02 | 16.4 | 29.5 | 570 | 5.0 | 21.8 | 1225 | 17.2 | 10.6 |
| 31 | Sarpifan ® VT | 4.47 | 9.0 | 21.5 | 635 | 3.8 | 20.2 | 1490 | 15.8 | 10.0 |
| 32 | Sarpifan ® WRG | 4.47 | 13.7 | 30.4 | 670 | 3.0 | 28.0 | 1280 | 16.0 | 9.8 |

EXAMPLES 33–37

50 g of a latex dispersion, 3 g of Mirox®TA, and 5 g of deionized water are made into a paste. Half of this paste is spread out over an area of 1000 cm² and dried at 160° C. for 1 minute in the circulating air drier. Then, the second half of the paste is spread out the resultant film, and 20 g of Favor®SXM 100 are sprinkled thereon. This body is heated to 160° C. for 1 minute. A foam of 30 g of the same latex dispersion, 3 g of Plantaren® 2000 CS/UP, and 10 g of water are expanded in the known manner to a foam weight per liter of about 250 g/l. This mass is evenly distributed on the produced body and immediately heated for 1 minute in the IR-field (10 kW/m²). Heating to 150° C. for 5 minutes test in the drying oven follows.

The absorption rate for synthetic urine is determined by means of DAT and DATP using 100 cm² pieces each time. In this case it is necessary that the foam layer lies on the liquid outlet since the layer manufactured with the paste is impermeable to liquid.

| Example [No.] | Dispersion [kind] | DAT [1'] [g] | DAT [5'] [g] | DATP [1'] [g] | DATP [5'] [g] | DATP [10'] [g] |
|---|---|---|---|---|---|---|
| 33 | Bunatex ® SL 3510 | 23.2 | 46.1 | 9.8 | 30.5 | 41.6 |
| 34 | Bunatex ® SL 2810 | 20.2 | 42.2 | 6.2 | 19.7 | 31.8 |
| 35 | Sarpifan ® WRG | 16.8 | 42.5 | 2.2 | 2.2 | 2.2 |
| 36 | Acronal ® DS 2331 X | 16.8 | 38.6 | 7.6 | 21.8 | 31.6 |
| 37 | Sarpifan ® NL | 17.7 | 45.5 | 6.0 | 25.1 | 34.5 |

EXAMPLES 38–42

A foam is prepared (foam weight per liter=350 g/cm²) from a foam of 0.3 g of Plantaren®2000 CS/UP, 0.6 g of Bunatex®SL 3510, 0.6 g of VP-Non-Gel, and 3.0 g of deionized water and spread on an area of 300 cm². The foam is sprinkled with 3 g of Favor®SXM 100, treated in the IR-field for 1 minute, and then heated in the drying oven for a certain time at a defined temperature. Then, a cover layer of the same foam is applied and the after-treatment repeated.

50 cm² pieces of these bodies are each examined in the DAT with respect to their absorption rate. To this end, the absorption after one, two, three, and four minutes, and the time required to absorb 50 ml of the solution are noted.

| Example [No.] | Temperature/Time [°C.]/[min.] | DAT [1'] [g] | DAT [2'] [g] | DAT [3'] [g] | DAT [4'] [g] | [50 g reached] [sec.] |
|---|---|---|---|---|---|---|
| 38 | 100/12 | 11.5 | 26.8 | 39.2 | 47.3 | 270 |
| 39 | 120/10 | 17.6 | 32.4 | 42.5 | 45.1 | 250 |
| 40 | 140/8 | 23.4 | 46.0 | 50.0 | 50.0 | 140 |
| 41 | 160/6 | 21.7 | 41.8 | 50.0 | 50.0 | 165 |
| 42 | 180/4 | 22.5 | 42.8 | 50.0 | 50.0 | 150 |

EXAMPLES 43–46

Bodies are prepared according to the same method as in the preceding Examples; however, differing amounts of VP-Non-Gel are added to the foams. All foams are heated to 140° C. for 8 minutes. The bodies are tested as in Examples 38–42.

| Example [No.] | VP-Non-Gel [g/foam layer] | DAT [1'] [g] | DAT [2'] [g] | DAT [3'] [g] | DAT [4'] [g] | [50 g reached] [sec.] |
|---|---|---|---|---|---|---|
| 43 | 0 | 22.9 | 31.7 | 37.2 | 42.2 | 350 |
| 44 | 0.6 | 20.4 | 39.2 | 44.4 | 48.0 | 290 |
| 45 | 1.2 | 24.3 | 42.5 | 50.0 | 50.0 | 165 |
| 46 | 2.4 | 7.8 | 17.7 | 29.5 | 38.8 | 345 |

EXAMPLE 47–50

Example 45 is repeated; however, differing amounts of titanium dioxide (Rutil-type) are incorporated as filler into each foam layer.

| Example [No.] | Titanium dioxide [g] | DAT [1'] [g] | DAT [2'] [g] | DAT [3'] [g] | [50 g reached] [sec.] |
|---|---|---|---|---|---|
| 47 | 0.6 | 18.1 | 37.0 | 50.0 | 155 |
| 48 | 1.2 | 22.1 | 43.6 | 50.0 | 135 |
| 49 | 2.4 | 22.6 | 43.7 | 50.0 | 145 |
| 50 | 4.8 | 12.8 | 25.1 | 38.8 | 220 |

EXAMPLES 51–54

The preceding Examples are repeated, except that 2.4 g of differing fillers are incorporated into the foams.

| Example [No.] | Filler [kind] | DAT [1'] [g] | [2'] [g] | [3'] [g] | [4'] [g] | [50 g reached] [sec.] |
|---|---|---|---|---|---|---|
| 51 | bentonite | 16.0 | 32.3 | 50.0 | 50.0 | 170 |
| 52 | chalk | 22.2 | 45.2 | 50.0 | 50.0 | 130 |
| 53 | Kaolin ® W | 1.5 | 2.9 | 4.3 | 7.0 | — |
| 54 | talc | 21.5 | 40.9 | 50.0 | 50.0 | 145 |

EXAMPLE 55, 56

Experiment 52 is repeated using 4.8 and 10 g of chalk as filler. In the DAT, the test pieces have an absorption of 50 ml after 120 and 105 seconds, respectively.

EXAMPLES 57–59

Experiment 52 is repeated; except that the amount of Favor® SXM 100 is increased to 300 g/m$^2$; in addition, the concentration of the chalk in the foam is further increased. Test pieces of 33.3 cm$^2$ are tested in the DATP. The liquid amount absorbed after fixed periods, and the time until 50 ml of test urine solution are absorbed served as test criteria.

| Example [No.] | Chalk [g/fo. lay.] | DATP [1'] [g] | [2'] [g] | [3'] [g] | [4'] [g] | [5'] [g] | [50 ml reached] [sec.] |
|---|---|---|---|---|---|---|---|
| 57 | 9.6 | 16.5 | 28.3 | 35.5 | 41.0 | 44.9 | 350 |
| 58 | 14.5 | 23.6 | 38.7 | 47.4 | 50.0 | 50.0 | 290 |
| 59 | 19.3 | 15.5 | 27.1 | 35.5 | 41.2 | 45.5 | 165 |

EXAMPLE 60

20 g of Estekoll® HL 40 are spread on a 500 cm$^2$ piece of polyethylene film (1.8 g); this layer is evenly sprinkled with 15 g of Favor®D SXM 100. This mass is dried at 100° C. for 10 minutes. Subsequently, a foam of 0.5 g of Plantaren®2000 CS/UP, 10 g of Bunatex®SL 3510, 2 g of VP-Non-Gel, and 5 g of deionized water is prepared (weight of foam per liter about 250 g/l); 8.05 g of chalk are additionally incorporated into this foam. The mass from the drying oven is evenly spread with this foam; this body is then aftertreated for 1 minute in the IR-field first and then 10 minutes at 100° C. in the drying oven.

In the DAT, a piece of this body having an area of 33.3 cm$^2$ has an absorption of 50 ml synth.urine after 9 minutes. The applied polyethylene film is impermeable to liquids, i.e., the DAT-test is conducted such that the foam layer is in contact with the liquid.

EXAMPLE 61

Procedure as in Example 60; however, a mixture of 10 g of Estekoll® HL 40, 10 g of water, and 2.5 g of Mirox® TA is applied on the polyethylene film as base layer. In addition, another foam layer having the same formulation is applied.

In the DAT, a 33.3 cm$^2$ piece of this body has an absorption of 50 ml synth. urine solution after 4.25 minutes.

EXAMPLE 62, 63

Example 58 was repeated; however, Neogel® V 70 ZB and Neogel® V 77 ZB, respectively, were used instead of the Non-Gel-Paste. In case of Neogel®V 70 ZB, the test substance had an absorption of 50 ml synth. urine (DAT) after 230 seconds, and in case of Neogel® V 77 ZB after 200 seconds.

EXAMPLES 64–71

1.7 g of Plantaren®2000 CS/UP, 5.21 g of Neogel®V 70 ZB, 13.02 g of deionized water are mixed with a polymer dispersion and expanded to about 300 g/l. Subsequently, a filler is optionally mixed into the foam. Then this is spread out over an area of 1302 cm$^2$ and sprinkled with 39.06 g of Favor®SXM 100. The mass is then heated for 4 minutes at 180° C. in the drying oven, spread another time with the same foam layer, and again dried at 180° C. for 4 minutes. Pieces having a size of 10×30 cm are cut out of the resultant body; the surface test is conducted with these pieces.

| Example | Dispersion/Amount | Filler/Amount |
|---|---|---|
| 64 | Bunatex ® SL 3510/26.04 g | —/— |
| 65 | Sarpifan ® MKD/35.41 g | —/— |
| 66 | Bunatex ® SL 3510/26.04 g | chalk/82.39 g |
| 67 | Bunatex ® SL 3510/26.04 g | Calcicoll ® W12/82.39 g |
| 68 | Sarpifan ® MKD/35.41 g | chalk/82.39 g |
| 69 | Bunatex ® SL 3510/26.04 g | chalk/41.2 g |
| 70 | Bunatex ® SL 3510/26.04 g | Calcicoll ® W 12/41.2 g |
| 71 | Sarpifan ® MKD/35.41 g | chalk/41.2 g |

| Ex. | -1- OA [ml] | -1- ZA [s] | -1- AV [ml] | -2- OA [ml] | -2- ZA [s] | -2- AV [ml] | -3- OA [ml] | -3- ZA [s] | -3- AV [ml] | -4- OA [ml] | -4- ZA [s] | -4- AV [ml] | -5- OA [ml] | -5- ZA [s] | -5- AV [ml] |
|---|---|---|---|---|---|---|---|---|---|---|---|---|---|---|---|
| 64 | 0.5 | 0 | 43 | 0 | 20 | 21 | 0 | 25 | 21 | 0 | 25 | 32 | 0 | 20 | 55 |
| 65 | 0 | 20 | 10 | 0 | 25 | 2 | — | — | — | — | — | — | — | — | — |
| 66 | 0 | 15 | 23 | 0 | 45 | 5 | 0 | 40 | 15 | 0 | 40 | 29 | 0 | 30 | 63 |
| 67 | 0 | 40 | 3 | 0 | — | 0 | 0 | — | 0 | 0 | 30 | 0.5 | — | — | — |
| 68 | 14 | — | 14 | 0 | — | 0 | 0 | — | 0 | 0 | 300 | 5 | — | — | — |
| 69 | 1 | 0 | 32 | 0 | 20 | 15 | 0 | 35 | 20 | 0 | 40 | 35 | 0 | 30 | 52 |
| 70 | 0.5 | 0 | 33 | 0 | 30 | 18 | 0 | 30 | 25 | 0 | 40 | 32 | 0 | 35 | 55 |
| 71 | 0 | 15 | 14 | 0 | — | 0 | 0 | — | 0 | 0 | 60 | 25 | — | — | — |

EXAMPLES 72–75

0.48 g of Plantaren®2000 CS/UP, 0.17 g of magnesium chloride (×6 H$_2$O), 2.38 g of deionized water are expanded with 6.48 g of Sarpifan®MKD, 0.33 g Fixapet®VNF, and chalk to about 300 g/l (calculated without chalk). This foam is spread on a surface of 14 ×34 cm and sprinkled with 4.5 g of Favor®SXM 100 on an area 10×30 cm. The mass is then heated for 3 minutes at 180° C. in drying oven, covered another time with the same foam layer, sprinkled once again with the same amount of Favor®SXM 100, and dried again at 180° C. for 3 minutes. A cover layer of the same foam material is spread thereon and oven-dried for the third time at 180° C. (cf. FIG. 1).

Subsequently, the samples are calendered.

| Ex. | Chalk [g] | -1- OA [ml] | -1- ZA [s] | -1- AV [ml] | -2- OA [ml] | -2- ZA [s] | -2- AV [ml] | -3- OA [ml] | -3- ZA [s] | -3- AV [ml] | -4- OA [ml] | -4- ZA [s] | -4- AV [ml] |
|---|---|---|---|---|---|---|---|---|---|---|---|---|---|
| 72 | 5.71 | 0 | — | 0 | 0 | 30 | 0.1 | 0 | 30 | 18 | 0 | 20 | 62 |
| 73 | 3.81 | 0 | — | 0 | 7.0 | 15 | 11 | 0 | 30 | 19 | 0 | 20 | 60 |
| 74 | 1.90 | 0 | 40 | 0.5 | 24 | 0 | 25 | 13 | 5 | 18 | 23 | 10 | 58 |
| 75 | 0.00 | 0 | 20 | 11 | 28 | 5 | 30 | 45 | 5 | 47 | 52 | 5 | 54 |

EXAMPLES 76–93

0.50 g of Plantaren®2000 CS/UP, 0.09 g of magnesium chloride (×6 H$_2$O), 2.4 g deionized water are expanded with 3.2 g of Sarpifan®MKD, 0.17 g of Fixapet®VNF, and 5.44 same foam layer, sprinkled once again with the same amount of Favor®SXM 100, and dried once more at 180° C. for 3 minutes. A cover layer of the same foam material is spread thereon and oven-dried for the third time at 180° C. Then the samples are calendered (unless stated otherwise).

| Example No. | Polymer dispersion | Initial weight | Remarks |
|---|---|---|---|
| 76 | Fixamin ® PUK | 3.20 g | |
| 77 | Sarpifan ® BKF | 3.20 g | unstable |
| 78 | Sarpifan ® CAW | 3.20 g | |
| 79 | Sarpifan ® DFP | 2.67 g | |
| 80 | Sarpifan ® HP79 | 3.08 g | |
| 81 | Sarpifan ® NL | 3.56 g | |
| 82 | Sarpifan ® U 75 | 3.20 g | |
| 83 | Sarpifan ® VBA | 3.20 g | |
| 84 | Sarpifan ® VT | 3.56 g | |
| 85 | Sarpifan ® WRG | 3.56 g | |
| 86 | Estekoll ® 60 | 2.67 g | |
| 87 | Estekoll ® HL 40 | 2.91 g | |
| 88 | Bunatex ® SL 2800 | 2.39 g | |
| 89 | Bunatex ® SL 3510 | 2.35 g | |
| 90 | Acronal ® DS 2331 X | 3.59 g | |
| 91 | Vinipas ® LL 778/5 | 3.20 g | |
| 92 | Lipolan ® VD 9910 | 3.20 g | not calendered |
| 93 | Litex ® AP 4120 | 3.20 g | |

| Ex. | -1- OA [ml] | -1- ZA [s] | -1- AV [ml] | -2- OA [ml] | -2- ZA [s] | -2- AV [ml] | -3- OA [ml] | -3- ZA [s] | -3- AV [ml] | -4- OA [ml] | -4- ZA [s] | -4- AV [ml] | -5- OA [ml] | -5- ZA [s] | -5- AV [ml] |
|---|---|---|---|---|---|---|---|---|---|---|---|---|---|---|---|
| 76 | 0 | 100 | 2 | 3.0 | 5 | 5 | 0 | 45 | 16 | 0 | 30 | 60 | 0 | 30 | 77 |
| 77 | — | — | — | — | — | — | — | — | — | — | — | — | — | — | — |
| 78 | 0 | — | 0 | 0 | — | 0 | 0 | 30 | 15 | 0 | 20 | 60 | 0 | 20 | 78 |
| 79 | 0 | 45 | 3 | 15 | 10 | 18 | 0 | 30 | 18 | 0 | 30 | 52 | 0 | 30 | 76 |
| 80 | 0 | — | 0 | 0 | 15 | 8 | 0 | 25 | 18 | 0 | 30 | 52 | 0 | 30 | 75 |
| 81 | 0 | — | 0 | 0 | — | 0 | 0 | 120 | 4 | 0 | 45 | 47 | 0 | 45 | 76 |
| 82 | 0 | — | 0 | —* | — | — | — | — | — | — | — | — | — | — | — |
| 83 | 0 | — | 0 | 0 | — | 0 | 0 | 70 | 9 | 0 | 30 | 55 | 0 | 30 | 80 |
| 84 | 10 | 15 | 23 | 34 | 0 | 37 | 28 | 0 | 35 | 20 | 0 | 45 | 16 | 15 | 67 |
| 85 | 0 | — | 0 | 0 | — | 0 | 0 | 60 | 10 | 0 | 30 | 58 | 0 | 30 | 77 |
| 86 | 0 | — | 0 | 0 | 40 | 1 | 0 | 45 | 15 | 0 | 30 | 56 | 0 | 20 | — |
| 87 | 0 | 35 | 1 | 14 | 5 | 17 | 0 | 30 | 20 | 0 | 20 | 60 | — | — | — |
| 88 | 10 | — | 10 | 3 | 15 | 7 | 0 | 30 | 13 | 0 | 20 | — | — | — | — |
| 89 | 14 | 0 | 30 | 0 | 30 | 4 | 0 | 30 | 10 | 0 | 30 | — | — | — | — |
| 90 | 0 | 30 | 18 | 6 | 10 | 12 | 0 | 30 | 14 | — | — | — | — | — | — |
| 91 | 0 | 45 | 6 | 0 | 20 | 8 | 0 | 45 | 20 | — | — | — | — | — | — |
| 92 | 0 | 10 | 65 | 0 | 20 | 36 | 0 | 30 | 32 | — | — | — | — | — | — |
| 93 | 0 | 40 | 2 | 0 | 35 | 1 | 0 | 35 | 18 | 0 | 25 | 56 | — | — | — |

*The experiments were terminated before the 5th run when the test body had torn the experiment.

g of chalk, and under the addition of a certain amount of a second polymer dispersion to about 300 g/l (calculated without chalk). Then this foam is spread on a surface of 14×34 cm and sprinkled with 4.5 g of Favor®SXM 100 on an area of 10×30 cm. This mass is then heated for 3 minutes at 180° C. in the drying oven, spread another time with the

EXAMPLES 94–96

A foam having a weigh per liter of 300 g/l is prepared from 8 g of Plantaren®2000 CS/UP, 8 g of Stokal®SR, x g of Sarpifan®VBA, 100 g of H$_2$O, and y g of Sarpifan®MKD. This is spread on an of 1 m$^2$, evenly sprinkled with 200 g of Favor®SXM 100, and then dried for 5 minutes at 160° C. A same foam layer is applied on this structure, evenly sprinkled with 100 g of Favor®SXM 100, and then dried again at 160° C. for 5 minutes.

Subsequently, the same foam layer is applied for two more times, followed by drying as above.

The absorption rate is determined after one minute in the DAT-test.

| Example No. | Sarpifan ® VBA [g/foam layer] | Sarpifan ® MKD [g/foam layer] | DAT (1 minute) [g/g] |
|---|---|---|---|
| 94 | 114.1 | 20.1 | 9.3 |
| 95 | 94.0 | 40.2 | 13.1 |
| 96 | 67.1 | 67.1 | 12.3 |

EXAMPLE 97

12.5 g of Plextol MV 604, 12.5 g of Plextol DV 440 (acrylate dispersions of Röhm GmbH), 1 g of Fixapret VNF, 0.1 g of magnesium chloride, 2 g of water, and 1 g of Glucosid 81 S (alkyl polyglycoside of Hüls AG, Marl) are mixed.

The mixture is expanded to a foam weight per liter of 40 g/l by means of a hand mixer. Half of the resulting foam is spread on surfaces of 40 * 50 cm and sprinkled with 40 g Favor SXM 100. The resultant structure is covered with the second half of the foam. Subsequently, drying for 4 minutes at 200° C. in circulating air drier follows. The resulting surface has a high flexibility. TBT (ret.): 6.6l(0.9% NaCl)/m².

EXAMPLE 98

Example 97 is repeated; however, prior to foaming, 2 g of the alkyl glycoside and 7.5 g of water are added additionally. The foam weight per liter of the foam prepared with this mixture amounts to 30 g/l.

The resultant sheet material has a coarser pore structure than that of Example 97, the absorption capacity amounts also to 6.6l/m².

We claim:

1. A layered body consisting of at least one foamed layer of plastic or latex and at least one layer of particulate superabsorbent polymer fixedly attached to a surface of at least one of said foamed layers by depositing particulate superabsorbent polymer on a wet polymer containing layer which is foamed to form the foamed layer to which surface the superabsorbent polymer particles are fixedly attached, said superabsorbent polymer being employed in a predetermined amount to cover at least a portion of said surface in a predetermined areal configuration, the quantity ratio of the foamed layer to the superabsorbent layer ranging from 1:500 to 50:1.

2. The layered body of claim 1 wherein said quantity ratio of the foamed layer to the superabsorbent polymer ranges from 1:5 to 10:1.

3. The layered body of claim 1 which has (1) a retention of at least 0.1 liter/m² surface, (2) a maximum absorption of at least 0.1 liter/m² surface, and (3) an absorption under load (AUL) of at least 2 g/g at 2.1 kPa with 0.9% NaCl solution.

4. A layered body consisting of at least one foamed layer of plastic or latex and at least one layer of particulate superabsorbent polymer fixedly attached to a surface of at least one of said foamed layers by depositing particulate superabsorbent polymer on a wet polymer containing layer which is foamed to form the foamed layer to which surface the superabsorbent polymer particles are fixedly attached, said superabsorbent polymer being employed in a predetermined amount to cover at least a portion of said surface in a predetermined areal configuration, the quantity ratio of the foamed layer to the superabsorbent layer ranging from 1:500 to 50:1, the layered body containing at least one filler in an amount of 0 to 1000% by weight based on the foamed layer.

5. The layered body of claim 4, wherein said amount of filler ranges from 0 to a maximum of 400 wt % relative to the amount of said foamed layer.

6. The layered body of claim 5, wherein said amount of filler ranges from 0 to a maximum of 200 wt % relative to the amount of said foamed layer.

7. The layered body of claim 4, wherein said filler is chalk, bentonite, silica gel, silicic acid, activated carbon, pigments, natural fibrous materials, synthetic fibrous materials or finely ground plastic materials.

8. The layered body of claim 7, wherein said filler is a pigment selected from the group consisting of titanium dioxide, iron oxide and combinations thereof.

9. The layered body of claim 7, wherein said fibrous material is viscose or cotton fibers or fabrics thereof, polyester or polyamide fibers, or combinations thereof or fibrous mixtures of said natural and synthetic fibrous materials.

10. The layered body of claim 1, where said one layer of particulate superabsorbent polymer is positioned between two foamed layers.

11. A layered body consisting of at least one foamed layer of plastic or latex and at least one layer of particulate superabsorbent polymer fixedly attached to a surface of at least one of said foamed layers by depositing particulate superabsorbent polymer on a wet polymer containing layer which is foamed to form the foamed layer to which surface the superabsorbent polymer particles are fixedly attached, said superabsorbent polymer being employed in a predetermined amount to cover at least a portion of said surface in a predetermined areal configuration, the quantity ratio of the foamed layer to the superabsorbent layer ranging from 1:500 to 50:1, the layered body on one side thereof being at least partially covered with a plastic film, fabric or combination thereof which is impermeable to aqueous liquids and water.

12. A method of preparing a hygienic article comprising: incorporating the layered body of claim 1, which imparts water or aqueous liquid absorbtivity to the hygienic article, among the other layers of said hygienic article.

13. The method of claim 12, wherein said hygienic article is diapers or incontinence articles.

14. The method of claim 12, wherein said layered body is a component of articles of clothing.

15. The use of the body which absorbs water and aqueous liquids according to claims 1, characterized in that it is used directly, or as a component in natural and/or artificial soils for plant cultivation or for the transport and storage of plants and parts of plants.

16. The use of the body which absorbs water and aqueous liquids according to claims 1, characterized in that it is used as insulating material for pipes and ducts, in particular for electric and light-transmitting cables.

17. The use of the body which absorbs water and aqueous liquids according to claims 1, characterized in that it is used as insulating material for constructional units, in particular in outer walls.

18. The use of the body which absorbs water and aqueous liquids according to claim 1, characterized in that it is used directly, or as a liquid-absorbing and/or liquid-storing component in packaging materials.

* * * * *